United States Patent [19]

Astier

[11] Patent Number: 5,039,948
[45] Date of Patent: Aug. 13, 1991

[54] APPARATUS FOR MEASURING ELECTROMAGNETIC CHARACTERISTICS OF A VERY HIGH TEMPERATURE MATERIAL

[75] Inventor: Jean-Pierre Astier, Pessac, France

[73] Assignee: Societe Europeenne de Propulsion, Suresnes, France

[21] Appl. No.: 526,047

[22] Filed: May 18, 1990

[30] Foreign Application Priority Data

May 22, 1989 [FR] France .................. 89 06660

[51] Int. Cl.⁵ .................. G01R 27/04; H01P 1/00
[52] U.S. Cl. .................. 324/642; 333/248
[58] Field of Search .................. 324/637, 642, 646; 333/248

[56] References Cited

U.S. PATENT DOCUMENTS

| | | | |
|---|---|---|---|
| 3,025,463 | 3/1962 | Luoma et al. | 324/58.5 |
| 3,233,172 | 2/1966 | Luoma | 324/642 |
| 3,939,415 | 2/1976 | Terasawa | 324/642 |
| 4,287,495 | 9/1981 | Lund, Jr. et al. | 333/239 |
| 4,704,576 | 11/1987 | Tributsch et al. | 324/642 |
| 4,949,034 | 8/1980 | Imura et al. | 324/642 |

FOREIGN PATENT DOCUMENTS 0172082 2/1986 European Pat. Off. .
1115129 5/1968 United Kingdom .

Primary Examiner—Kenneth A. Wieder
Assistant Examiner—Maura K. Regan
Attorney, Agent, or Firm—Weingarten, Schurgin, Gagnebin & Hayes

[57] ABSTRACT

The apparatus comprises a waveguide having one end with an outside rim in the form of a test flange having a plane front surface defining a calibration plane and intended to be applied against a plane surface of a sample of material to be tested, a generator coupled to the waveguide to inject microwaves therein, and means for detecting the waves reflected by the material. At least the terminal portion of the waveguide including the test flange for application against the material to be tested at very high temperature is made of an electrically conductive refractory composite material, such as a carbon/carbon or a carbon/ceramic composite material.

4 Claims, 1 Drawing Sheet

APPARATUS FOR MEASURING ELECTROMAGNETIC CHARACTERISTICS OF A VERY HIGH TEMPERATURE MATERIAL

The present invention relates to measuring electromagnetic characteristics of a material, in particular its complex permittivity.

BACKGROUND OF THE INVENTION

Various methods of measuring the complex permittivity of a dielectric material are known. Some methods use a waveguide, a coaxial line, or a resonant cavity loaded with the material to be tested. Another known method uses a waveguide radiating into the material to be tested.

In some cases, it is necessary to measure electromagnetic characteristics on materials raised to very high temperature, i.e. to more than 1000° C. This applies, in particular, to dielectric materials which are heated to a large extent in use, e.g. the materials used for the outside portions of aircraft or other air or space vehicles.

The known methods are unsuitable when measurements need to be performed on a material raised to high temperature. Because of thermal deformation, this applies in particular to putting a waveguide into contact with the material to be tested. In addition, heat losses by contact with the waveguide prevent a uniform temperature being obtained within the material under test.

Thus, the object of the present invention is to provide an apparatus which is particularly suitable for measuring electromagnetic characteristics of a material at very high temperature.

SUMMARY OF THE INVENTION

This object is achieved by means of an apparatus for measuring electromagnetic characteristics of a very high temperature material, the apparatus comprising a waveguide having one end with an outside rim in the form of a test flange having a plane front surface defining a calibration plane and intended to be applied against a plane surface of a sample of material to be tested, a generator coupled to the waveguide to inject microwaves therein, and means for detecting the waves reflected by the material, wherein at least the terminal portion of the waveguide including the test flange for application against the material to be tested at very high temperature is made of an electrically conductive refractory composite material.

Preferably, the terminal portion of the waveguide is made of a composite selected from carbon/carbon and carbon/ceramic, i.e. a composite constituted by fibrous carbon reinforcement in a matrix of carbon or of a ceramic material such a silicon carbide.

By using a terminal portion made of a refractory composite, the reference of the calibration plane can be conserved because of the thermal stability of the composite. In addition, the thermally insulating nature of the composite prevents a heat flow bridge being established between the material and the waveguide.

BRIEF DESCRIPTION OF THE DRAWING

An embodiment of the invention is described by way of example with reference to the accompanying drawing, in which.

DETAILED DESCRIPTION

Figure 1:
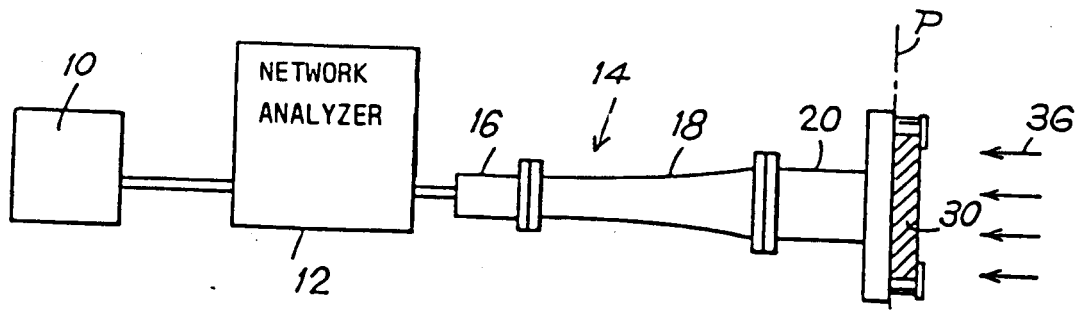
FIG. 1 is an overall diagram of measurement apparatus in accordance with the invention.

As shown in FIG. 1, the measurement apparatus comprises a microwave generator 10 coupled to a waveguide 14 within which waves propagate up to its end and from which they radiate into a sample 30 of material to be tested. A network analysis system 18, e.g. equipment sold under the reference 8 510 by the U.S. firm Hewlett-Packard, is interposed between the generator 10 and the waveguide 14 in order to detect the waves reflected by the material under test for the purpose of determining the phase and amplitude of its reflection factor, thereby making it possible to deduce the complex permitivity of the material under test. The theory of such measurement apparatus is well known, so a more detailed description is not needed.

Figure 2:
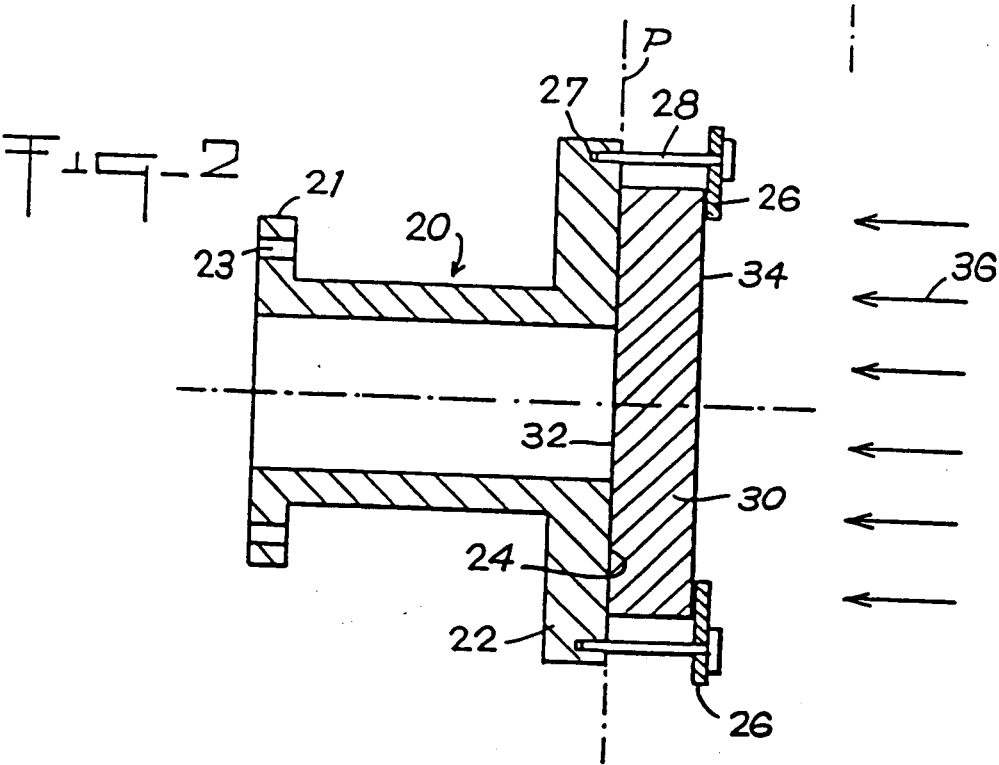
FIGS. 2 and 3 are more detailed views, respectively an axial section and an end view, showing the terminal portion of the waveguide which is applied against a sample of material to be tested.
Figure 3:
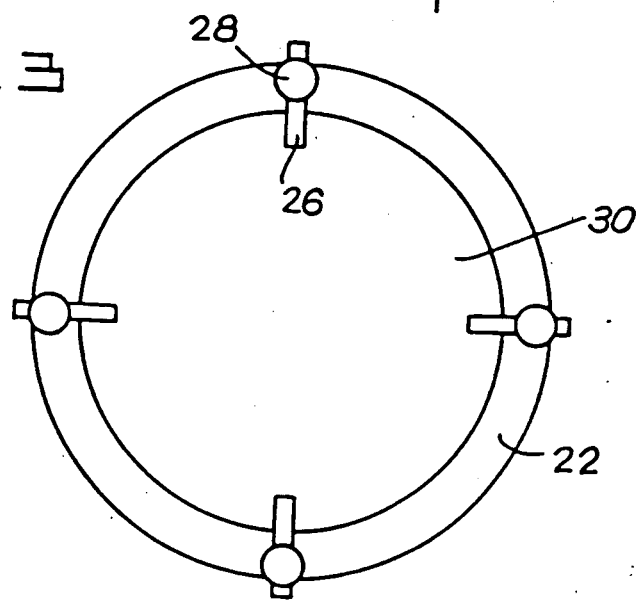

The terminal portion of the waveguide 14, as shown in detail in FIGS. 2 and 3, is circular and is constituted by a portion 20 provided at its end with an outwardly directed annular rim constituting a test flange 22. The front plane surface 24 of the test flange 22 defines a calibration plane P. The sample 30 of material to be tested is constituted by a test piece in the form of a disk having one of its plane surfaces 32 applied against the test flange 22 and consequently situated in the calibration plane.

In order to perform measurements at high temperature, the sample 30 is subjected to heat flux 36 directed towards its surface 34 opposite to its surface 32. The heat flux is produced by a heat source, e.g. a solar furnace (not shown).

The sample 30 is held against the test flange 22 by means of fingers 26 bearing against the face 34 of the sample 30 and fixed to the test flange 22 by screws 28, there being four such fingers in the example shown.

The terminal part 20 of the waveguide is made of a refractory composite material, preferably a material reinforced by carbon fibers and having a matrix of carbon or of ceramic, e.g. silicon carbide. Such a material is electrically conductive, has a high degree of thermal stability, and retains its mechanical properties at high temperatures.

At its end opposite to that constituted by the part 20, the waveguide 14 is constituted by a length 16 of rectangular section connected to the terminal part 20 by means of a standard rectangular waveguide to circular waveguide transition 18. The various pieces constituting the waveguide 14 are interconnected by coupling flanges.

The terminal part 20 may be manufactured as follows, for example. A fiber preform of the part 20 is made by winding a strip of cloth on a mandrel in order to form the tubular portion of the part 20, and a tape of the same cloth is wound to form the test flange 22 and the coupling flange 21 for engaging the transition part 18. The layers of cloth may be held together by needling. The preform made in this way is densified by chemical vapor infiltration of the matrix material, e.g. silicon carbide. A method of making a carbon/silicon carbide composite is described, for example, in European patent EP 0 172 082. After densification, the part 20 is machined, in particular to rectify its inside cylindrical surface, its front surface 24, and the end surface of its coupling flange 21, and also to form holes 27 in the test flange 22 for receiving the screws 28, and holes 23 in the coupling flange 21 for connection with the transition part 18.

Advantageously, the fingers 26 for holding the sample 30 are also made of refractory composite material, e.g. a carbon/silicon carbide composite, and provided with antioxidation protection in order to conserve adequate mechanical properties at the high temperatures to which the sample is exposed. As shown in the figures, the fingers 26 bear against the periphery of the sample 30 in such a manner as to avoid disturbing the electromagnetic field lines in the material under test.

In order to perform a measurement, the sample of material to be tested is placed at the end of the waveguide 20 and is subjected to the heat flux 36 in order to raise the sample 30 to the desired temperature, e.g. higher than 1000° C.

The microwaves produced by the generator 10 propagate in fundamental $TE_{11}$ mode along the waveguide 14 and radiate into the sample 30. The inside diameter of the terminal portion 20 is designed to be suitable for propagating microwaves, e.g. at a frequency lying in the range 2 GHz to 40 GHz. The network analyzer 12 gives the value of the reflection factor in phase and amplitude, i.e. the reflection coefficient for $TE_{11}$ mode, thereby enabling the complex permittivity to be deduced.

The measurement system is initially calibrated by placing a series of short circuits offset by wavelengths \g/12, \g/4, and 5 \g/12 (where \g is the guided wavelength) relative to the plane P at the end of the waveguide 14, and by performing the necessary adjustments in order to obtain a reflection coefficient with attenuation of 0 dB and a phase shift of 180°.

Several significant advantages are obtained by using a terminal part 20 made of a refractory composite material which, in addition to its properties of electrical conductivity and mechanical strength at high temperature, also has a high degree of dimensional stability when subjected to temperature variations and constitutes a thermal insulator. These advantages make it possible to perform measurements at very high temperatures, above 1000° C., and even above 2000° C.

Thus, its dimensional stability makes it possible to keep the position of the calibration plane unchanged between initial adjustment and having a sample 30 at very high temperature bearing against the test flange 22. This would not be true of a terminal part made of metal, e.g. copper, because thermal expansion would give rise to substantial errors in measurement. Further, thermal expansion would also deform the front face of the test flange 22 and would consequently give rise to poor contact between the test flange and the sample.

Further, the thermal insulation property prevents heat being transferred across the interface from the sample 30 to the test flange 22, where such test transfer would give rise to a temperature gradient within the sample material. The apparatus of the invention thus makes it possible to conserve uniform temperature within any material irradiated by the microwaves.

I claim:

1. Apparatus for measuring electromagnetic characteristics of a material at a temperature of at least 1000° C., the apparatus comprising a waveguide having one end with an outside rim in the form of a test flange having a plane front surface defining a calibration plane and adapted to be applied against a plane surface of a sample of material to be tested, a generator coupled to the waveguide to inject microwaves therein, and means for detecting the waves reflected by the material, wherein at least the terminal portion of the waveguide including the test flange adapted for application against the material to be tested at a temperature of at least 1000° C. is made of an electrically conductive refractory composite material.

2. Apparatus according to claim 1, wherein the terminal portion of the waveguide is made of a composite selected from carbon/carbon and carbon/ceramic.

3. Apparatus according to claim 1, further including holding parts connected to the test flange of the terminal portion of the waveguide and intended to hold a sample of material to be tested against the flange, said holding parts being made of a refractory composite material.

4. Apparatus according to claim 1, including means for exposing a sample of material to be tested to a thermal flux on its side opposite from its side applied to the test flange of the terminal portion of the waveguide.

* * * * *